United States Patent
Maeder et al.

(10) Patent No.: US 6,730,319 B2
(45) Date of Patent: May 4, 2004

(54) PHARMACEUTICAL COMPOSITIONS HAVING DEPRESSED MELTING POINTS

(75) Inventors: Karsten Maeder, Freiburg (DE); Lukas Christoph Scheibler, August (CH); Hans Steffen, Liestal (CH)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 10/154,554

(22) Filed: May 23, 2002

(65) Prior Publication Data

US 2003/0039686 A1 Feb. 27, 2003

(30) Foreign Application Priority Data

Jun. 6, 2001 (EP) .............................. 01113792

(51) Int. Cl.$^7$ .......................... A61K 9/10; A61K 31/365
(52) U.S. Cl. ...................... 424/464; 424/465; 424/468; 424/474; 424/476; 424/451; 424/452; 424/489; 424/502; 424/501; 424/499; 424/456; 514/897
(58) Field of Search .......................... 424/464, 465, 424/468, 474, 476, 451, 452, 489, 502, 400, 456, 499, 501; 514/897

(56) References Cited

U.S. PATENT DOCUMENTS

| 4,540,602 A | 9/1985 | Motoyama et al. |
| 4,598,089 A | 7/1986 | Hadvary et al. |
| 5,145,684 A | 9/1992 | Liversidge et al. |
| 5,858,410 A | 1/1999 | Muller et al. |

FOREIGN PATENT DOCUMENTS

| DE | 32 17071 | 11/1983 |
| EP | 185 359 | 6/1986 |
| EP | 189 577 | 8/1986 |
| EP | 443 449 | 8/1991 |
| EP | 0465 423 | 1/1992 |
| EP | 524 495 | 1/1993 |
| EP | 901 792 | 3/1999 |
| WO | WO 99/33450 | 7/1999 |
| WO | WO 00/09122 | 2/2000 |
| WO | WO 00/09122 A1 * | 2/2000 |
| WO | WO 00/40569 | 7/2000 |
| WO | WO 01/19340 | 3/2001 |
| WO | WO 01/19340 A1 * | 3/2001 |
| WO | WO 01/19378 | 3/2001 |
| WO | WO 01/32616 | 5/2001 |
| WO | WO 01/32669 | 5/2001 |
| WO | WO 01/32670 | 5/2001 |

OTHER PUBLICATIONS

Kotsovolou et al., J. Org. Chem., 66, pp. 962–967 (2001).
Mutoh et al., J. of Antibiot., 47, pp. 1369–1375 (1994).
Charman et al., J. Pharm. Sci., 86, pp. 269–282 (1997).
Serajuddin, A., J. Pharm. Sci., 88, pp. 1058–1066 (1999).
Lander et al., Biotechnol. Prog., 16, pp. 80–85 (2000).

* cited by examiner

Primary Examiner—Thurman K. Page
Assistant Examiner—Rachel M. Bennett
(74) Attorney, Agent, or Firm—George W. Johnston; John P. Parise

(57) ABSTRACT

The present invention relates to pharmaceutical compositions that contain a solid pharmaceutically active compound having a melting point $\geq 37°$ C. and a fatty acid or a fatty acid salt or a mixture of a fatty acid and a fatty acid salt. Such composition results in a depression in melting point to $\leq 37°$ C. upon contact with an aqueous solution thereby providing an improved outlook for absorption.

28 Claims, 1 Drawing Sheet

PHARMACEUTICAL COMPOSITIONS HAVING DEPRESSED MELTING POINTS

BACKGROUND OF THE INVENTION

1. Field

The present invention relates to pharmaceutical compositions. More particularly, the invention relates to a solid pharmaceutical composition comprising a) a solid pharmaceutically active compound which has a melting point $\geq 37°$ C. and b) a fatty acid or a fatty acid salt or a mixture of a fatty acid and a fatty acid salt, characterized in that the constituents of a) and b) show a depression of their melting points to $\leq 37°$ C. upon contact with an aqueous solution.

2. Description

Many pharmaceutically active compounds exhibit low solubilities and low dissolution rates in the biological environment. Examples include cyclosporine, nifedipine, ritonavir, griseofulvin, ubidecarenone, danazol, halofantrine, and tetrahydrolipstatin. Because of the low solubility and the low dissolution rate of the pharmaceutically active compounds, only a certain percentage of the drug molecules is dissolved from the crystals. Undissolved drug crystals exhibit no or very limited therapeutic activity in most cases, independent whether a systemic action (requires drug absorption) or a localized effect (within the lumen of the gastrointestinal tract) is desired. Due to the low dissolution of the active compound, higher doses have to be administrated which might result in an increased danger of side effects. Furthermore it has been found that the presence of food might effect the dissolution, absorption and activity of the compound to a large extend. As an example, the bioavailability of alpha-tocopherol-nicotinate increased 28-fold in the fed status compared to the fasted state [William N. Charman et al., *J. Pharm. Sci*: 86, 269–282 (1997)]. Other examples include danazol, halofantrine and etretinate. It is obvious for those skilled in the art that the high impact of food on the dissolution of the drug leads to an unpredictable performance of the drug. However, a low variation of the drug dissolution is a necessity to achieve the desired concentration for the pharmaceutically effect and to avoid the toxic effects due to overdosing. A pharmaceutically active compound can only be accepted if a reliable pharmacokinetic profile can be achieved.

The need of the development of drug delivery systems to overcome the high variation of drug dissolution has been widely recognized. Approaches include the development of solid dispersions ("solid solution") [A. T. M. Serajuddin, *J. Pharm. Sci.*, 88, 1058-1066 (1999)]. The main disadvantage of this approach is the thermodynamic instability of the supersaturated solid dispersion, which might lead to crystallization processes leading to decreased dissolution velocities and unpredictable bioavailbilities.

Another approach to decrease the impact of food effects is the production of drug nanoparticules by wet-milling (U.S. Pat. Nos. 4,540,602 and 5,145,684) or High Pressure Homogenization (U.S. Pat. No. 5,858,410). However, disadvantages include the contamination of the product with abrasive material from the milling process. Furthermore, both processes require the presence of suspending liquids and the primary product is a nanosuspension and not dry nanoparticles. The prevention of the increase in particle size due to aggregation or Ostwald ripening is very challenging. Stabilization of the submicrometer sized particles often requires the time and cost intensive removal of the previously added suspension liquid by drying or cryodrying processes. Other disadvantages include the long processing time in wet milling (hours to several days) and the increase in temperature and the possible formation of radicals during the high pressure homogenization process [R. Lander et al., *Biotechinol. Prog.*, 16, 80–15(2000)]. Changes of drug modifications have also to be considered as a result of the milling processes.

It must also be kept in mind, that amorphous drug molecules and drug nanoparticles might degrade faster than the unprocessed material due to the increased surface area. Other approaches include the administration of the solubilized pharmaceutically active compound. However, this approach might lead to problems related to the chemical stability of the active compound, because degradation processes will occur more rapidly in the solubilized state compared to the crystalline state.

For example, lipase inhibitor molecules orlistat (tetrahydrolipstatin), or structurally related compounds, e.g. 2-oxy-4H-3,1-benzoxanzin-4-ones as described in WO00/40569, or 2-oxo amide triacylglycerol analogues [S. Kotsovolou et al., *J. Org. Chem.*, 66: 962–967 (2001)] are molecules that may degrade during storage by different mechanisms. It is well known that degradation velocity depends to a large extent from the physicochemical state of the active compound. In general, drug crystals have higher chemical stability compared to drug molecules in the amorphous or liquid state. Therefore, for good storage stability it is desirable to incorporate drug molecules in the crystalline form into the drug delivery system. It is, however, also well known, that in most cases pharmacoactivity is related to physicochemical states with high mobility, e.g. the solubilized or molten molecule. Therefore, from the point of pharmacoactivity, the drug molecule must be either given in a solubilized form or transform into a solubilized form within the body.

Both stability and activity aspects have to be considered. Therefore, the development of a drug-crystal loaded carrier which releases a solubilized drug is the most desirable case. This concept is easily realized for water-soluble drugs (e.g. ascorbic acid). However, the in situ transformation of poor water-soluble drugs remains a challenge.

The subject invention addresses this challenge.

SUMMARY OF THE INVENTION

The subject invention provides a solid pharmaceutical composition, which comprises a solid pharmaceutically active compound that has a melting point $\geq 37°$ C., and a fatty acid or a fatty acid salt or a mixture of a fatty acid and a fatty acid salt. The pharmaceutically active compound and the fatty acid or a fatty acid salt or a mixture of a fatty acid and a fatty acid salt are present in amounts such that when the composition is contacted with an aqueous solution having a pH value $\leq 8$, the melting point of the composition is less than the melting point of the solid pharmaceutically active compound and $\leq 37°$ C.

DETAILED DESCRIPTION OF THE PREFERRED EMBODIMENTS

Figure 1:
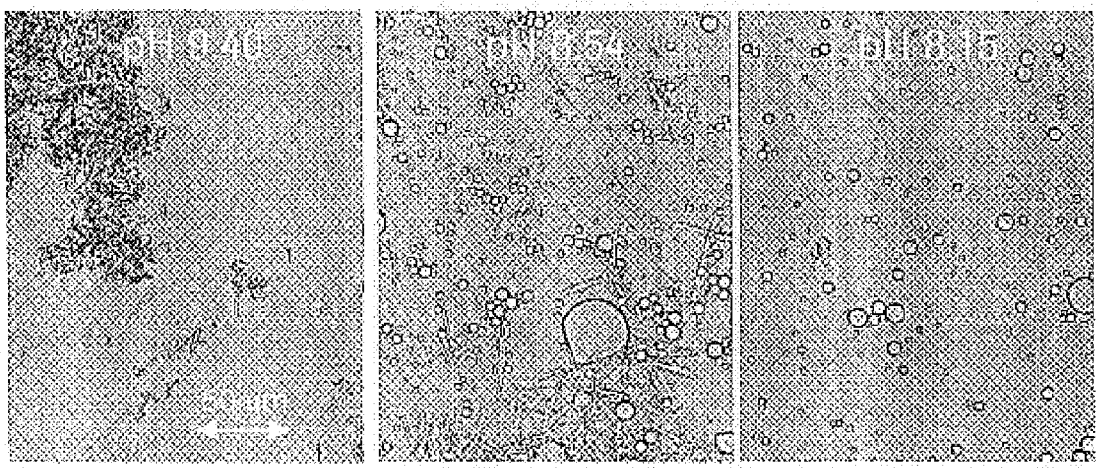
FIG. 1: Light-microscopic pictures of aqueous dispersions of orlistat/sodium laurate dispersions at varying pH-values (37° C.).

The subject invention will now be described in terms of its preferred embodiments. These embodiments are set forth to aid in understanding the invention but are not to be construed as limiting.

Surprisingly it has been found that fatty acids and/or fatty acid salts transform with pharmaceutically active compounds, preferably lipophilic compounds, into liquid droplets under conditions simulating the physiological environment. The pH-value plays a critical role in transforming a part of the fatty acid salt into the protonated fatty acid. Protonated fatty acids depress the melting point of certain lipophilic pharmaceutically active compounds, e.g. lipase inhibitors like orlistat, and are able to solubilize sufficiently amounts of the pharmaceutically active compound. Due to the eutectic interaction between the compounds, the melting point of both the lipophilic pharmaceutically active compound, e.g. orlistat with a melting point of 43° C. and the fatty acid drops below body temperature (<37° C.). Therefore, the lipophilic pharmaceutically active compound, e.g. orlistat, and the fatty acid are released in the liquid phase although their (individual) melting points may exceed the body temperature.

Accordingly, the present invention relates to a solid pharmaceutical composition comprising
   a) a solid pharmaceutically active compound which has a melting point ≧37° C. and
   b) a fatty acid or a fatty acid salt or a mixture of a fatty acid and a fatty acid salt, and
   c) optionally additional pharmaceutically acceptable excipients,
   characterized in that the constituents of a) and b) show a depression of their melting points to ≦37° C. upon contact with an aqueous solution.

This invention provides pharmaceutical compositions that are able to transform the active ingredient after oral ingestion from a solid form with a melting point of the active ingredients ≧37° C. to a liquid form, which is released. The manufacturing of the composition excludes the disadvantages of other formulation approaches, such as:
   the formation of supersaturated compositions (as in "solid solutions")
   high mechanical energy for particle disruption, which may lead to contamination with abrasive material (as by wet milling, high pressure homogenization) and/or radical formation
   the formation of different drug polymorphs or pseudopoylmorphs due to the processing
   increased degradation rates due to the liquid/semiliquid form of the active compound.

The in-situ transformation of the active compound into a liquid combines the advantages of good storage stability of drug crystals (no drug solubilization, no supersaturation, no radical formation due to particle disruption, preserved particle size) with the high activity of compositions which release the active molecule in the liquid form.

In the present invention the term "pharmaceutically acceptable" as used herein stands for that the buffer or salts are acceptable from a toxicity viewpoint.

The term "pharmaceutically acceptable salts" as used herein stands for salts of fatty acids with an organic or inorganic base such as ammonium hydroxide, diethanolammonium hydroxide, triethanolammonium hydroxide, (hydroxyethyl)ammonium hydroxide, sodium hydroxide, potassium hydroxide, etc. For the present compositions pharmaceutically acceptable salts of the fatty acids mentioned are sodium, potassium, magnesium and calcium salts, preferably sodium and potassium salts.

The term "pharmaceutically active compound" refers to molecules with low water solubility. Preferably the pharmaceutically active compound is a lipophilic compound, more preferably a lipase inhibitor and most preferably orlistat.

The term "fatty acid" comprises one single fatty acid as well as a mixture of two or more fatty acids as defined below.

The term "fatty acid salt" comprises one single fatty acid salt as well as a mixture of two or more fatty acid salts as defined below.

The term "lipophilic compounds," as defined herein, stands for compounds soluble in organic solvents. While the compounds suitable for use here may have minimal solubility in water, their solubility in organic solvents is substantially greater. Generally, the solubility of a lipophilic compound in a organic solvent should be high enough to prepare at least 1% solution of the compound in the organic solvent.

The composition shows "eutectic behavior" in that sense, that the melting point of the composition in the aqueous phase below pH 8 is lower than the melting point of each of the single components.

A "lipophilic compound" may be any lipophilic pharmaceutical active compound desirable in oral compositions as long as the compound satisfies the solubility requirements outlined above.

In a preferred embodiment of the present invention the pharmaceutically active compound has a melting point ≧37° C.

The pharmaceutically active compounds are characterized by low water solubility. Preferably, the pharmaceutically active compound is a lipophilic compound, e.g. orlistat. Examples for these compounds are antibiotics, lipophilic vitamins and their derivatives, and lipase inhibitors such as orlistat.

The term "lipase inhibitor" refers to compounds which are capable of inhibiting the action of lipases, for example gastric and pancreatic lipases, e.g. orlistat.

Orlistat (tetrahydrolipstatin) is a well known example for a lipase inhibitor (formula (I)).

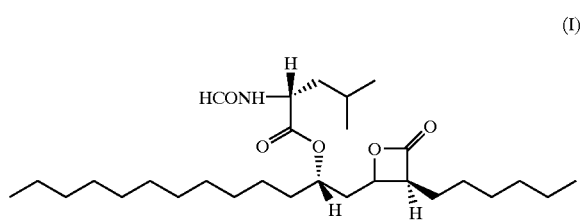

(I)

Orlistat is useful in the control or prevention of obesity and hyperlipidemia. See, U.S. Pat. No. 4,598,089, issued Jul. 1, 1986, which also discloses processes for making orlistat. Additional processes for the preparation of orlistat are disclosed in European Patent Applications Publication Nos. 185,359, 189,577, 443,449, and 524,495.

Other lipase inhibitors include a class of compound commonly referred to as panclicins. Panclicins are analogues of orlistat [Mutoh et al., *J. Antibiot.*, 47(12):1369–1375 (1994)]. In addition, the term "lipase inhibitor" also refers to 2-oxy-4H-3,1-benzoxazin-4-ones which have been described in International Patent Application WO00/40569 (Alizyme Therapeutics Ltd.), e.g. 2-decyloxy-6-methyl-4H-3,1-benzooxazin-4-one, 6-methyl-2-tetradecyloxy-4H-3,1-benzoxazin-4-one, and 2-hexadecyloxy-6-methyl-4H-3,1-benzoxazin-4-one and other oxetanones described for example in International Patent Applications WO01/32616, WO01/32669 and WO01/32670. Most preferably, the term "lipase inhibitor" refers to orlistat.

The preferred compositions have eutectic behavior in aqueous solutions at pH values $\leq 8$. An example for this kind of solution is buccal or gastric fluid.

In a further preferred embodiment of the present invention, the term "fatty acid or the fatty acid salt or the mixture of a fatty acid and a fatty acid salt" refers to $C_8$ to $C_{24}$, preferably a $C_{12}$ to $C_{18}$ saturated and non-saturated fatty acids, and salts thereof. The above term also refers to dicarboxylic acids and salts thereof. The corresponding fatty acid salts may be selected from the group consisting of the corresponding ammonium, bis(2-hydroxyethyl)ammonium, diethanolammonium, triethanolammonium, sodium, potassium, magnesium and calcium salt, preferably the corresponding sodium or potassium salt, and most preferably the corresponding sodium salt.

The fatty acids, fatty acids salts and mixtures thereof are known in the art and commercially available (DM Small: Handbook of lipid research. Vol. 4, Plenum Press New York, 1986; Fatty acid sources: Aldrich, Sigma, Fluka, Karlshamns, Indofine, Cognis, Croda).

The preparation of mixtures of fatty acids, of fatty acids salts and of fatty acids and fatty acids salts may be performed according to methods known in the art, e.g. dry mixing, melting with or without solvent, etc.

In a preferred embodiment of the present invention the fatty acid or a fatty acid salt or the mixture of a fatty acid and a fatty acid salt may be selected from $C_8$ to $C_{24}$, preferably a $C_{12}$ to $C_{18}$ saturated fatty acids and salts thereof, e.g. selected from the group of a consisting of lauric acid, myristic acid, palmitic acid, stearic acid, arachidic acid and behenic acid; more preferably lauric acid, myristic acid and palmitic acid, and most preferably lauric or myristic acid and salts thereof.

In a further preferred embodiment of the invention the fatty acid or a fatty acid salt or the mixture of a fatty acid and a fatty acid salt may be selected from $C_8$ to $C_{24}$, preferably a $C_{12}$ to $C_8$, mono-or polyunsaturated fatty acids and salts thereof, e.g. selected from the group consisting of palmitoleic acid, oleic acid, elaidic acid, erucic acid, linoleic acid, gamma-linolenic acid, alpha-linolenic acid and arachidonic acid, preferably oleic acid or linoleic acid and salts thereof.

Further, the fatty acid or a fatty acid salt or the mixture of a fatty acid and a fatty acid salt may be selected from dicarboxylic acids from $C_5$ to $C_{24}$, e.g. glutaric acid, adipic acid, pimelic acid, suberic acid, azelaic acid, sebacic acid, dodecanedioc acid, and tetradecandioic acid and/or a salt thereof.

The fatty acid (or the corresponding salt) may comprise one single fatty acid (or the corresponding salt) as well as a mixture of two or more fatty acids (or the corresponding salts) as described above.

The corresponding fatty acid salt may be an ammonium, bis(2-hydroxyethyl)ammonium, diethanolammonium, triethanolammonium, sodium, potassium, magnesium or calcium salt, preferably a sodium or potassium salt.

The preferred ratio (w/w) between pharmaceutically active compound and fatty acid or a fatty acid salt or a mixture of a fatty acid and a fatty acid salt is as follows: The composition may comprise 0.05 mg to 20 mg fatty acid or 0.05 mg to 20 mg fatty acid salt or 0.05 mg to 20 mg of a mixture of a fatty acid and a fatty acid salt is used per 1 mg pharmaceutically active compound. Preferably the composition comprises 0.5 mg to 2 mg fatty acid or 0.5 mg to 2 mg fatty acid salt or 0.5 to 2 mg of a mixture of a fatty acid and a fatty acid salt is used per mg pharmaceutically active compound. The preferred pharmaceutically active compound in this composition is a lipase inhibitor, most preferably orlistat.

In case in addition to the effect of a lipase inhibitor an additional inhibition of gastric lipases should be achieved a higher amount of fatty acids/fatty acid salts may be advisable. This additional inhibition of gastric lipases by providing additional fatty acids or fatty acids salts or a mixture of at least one fatty acid and at least one fatty acid salt is known in the art and has been described e.g. in European Patent Application No. 901,792 and German Patent Application No. 3,217,071. In this case the ratio between lipase inhibitor and fatty acid or fatty acid salt and a mixture of fatty acid salt may change to up to 1:20 (w/w).

For lipase inhibitors as described above, e.g. orlistat, preferred compositions comprise 10 to 240 mg, more preferably 40 to 120 mg, e.g. 40, 60, 80, 100, or 120 mg.

Especially preferred compositions comprise 60 to 120 mg orlistat and 30 mg to 100 mg fatty acid or fatty acid salt or a mixture of fatty acid and fatty acid salt. For example a composition as defined above may comprise 120 mg orlistat and 60 mg fatty acid or fatty acid salt or a mixture of a fatty acid and a fatty acid salt.

Each dosage unit of the above pharmaceutical compositions can obtain the daily doses of the pharmaceutically active compound or may contain a fraction of the daily dose, such as one-third of the doses. Alternatively, each dosage unit may contain the entire dose of one of the compounds, and a fraction of the dose of the other compound. In such case the patient would daily take one of the combination dosage units, and one or more units containing only the other compound.

Orlistat is preferably orally administered from 30 to 800 mg per day in divided doses two to three times per day. Preferred is wherein from 120 to 240 mg, most preferably 180 mg per day of a lipase inhibitor is administered to a subject, preferably in divided doses two or, particularly, three times per day. Generally, it is preferred that the lipase inhibitor has to be administered within about one or two hours of ingestion of a meal containing fat. Generally, for administering a lipase inhibitor as defined above it is preferred that treatment be administered to a human who has a strong family history of obesity or has obtained a body mass index of 25 or greater.

The compositions of the present invention may be administered to humans in conventional oral compositions, such as, tablets, coated tablets, hard and soft gelatin capsules, emulsions or suspensions. Examples of carriers which can be used for tablets, coated tablets, dragées, hard gelatin capsules and sachets are lactose, other sugars and sugar alcohols like sorbitol, mannitol, maltodextrin, or other fillers; surfactants like sodium lauryl sulfate, Brij 96, Tween 80 or sucrose esters; disintegrants like sodium starch glycolate, maize starch or derivatives thereof; polymers like povidone, crospovidone; lubricants like talc; stearic acid or its salts and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art.

Especially, the above compositions may comprise one or more pharmaceutically acceptable excipients selected from the group consisting of mannitol, lactose, HPMC, talcum, sorbitol, polyvinylpyrrolidone, lecithin, trimyristine, polyethylenglycol, sucrose ester, polysorbate, polyoxethylenstearate, and dimethicone, preferably a sucrose ester, e.g. sucrosepalmitate and/or lactose.

Oral dosage forms are the preferred compositions for use in the present invention and these are the known pharmaceutical forms for such administration, for example tablets, capsules or sachets. The pharmaceutically acceptable excipients (diluents and carriers) are known in the pharmacist's art. Tablets may be formed from a mixture of the active compounds with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound with or without added excipients, may be prepared by known methods. The contents of the capsule may be formulated using known methods so as to give sustained release of the active compound. For example, the tablets and capsules may conveniently each contain the amounts of a pharmaceutically active compound and a fatty acid or a fatty acid salt or a mixture of a fatty acid and a fatty acid salt as described above.

The oral dosage form may be a chewable tablet comprising 10–240 mg of orlistat, 0.5–2000 mg of fatty acid or a fatty acid salt or a mixture of fatty acid salt with fatty acid, 5–200 mg of sucrosepalmitate and optionally 1.5 g of lactose.

In the compositions of the present invention the active compounds may, if desired, be associated with other compatible pharmacologically active ingredients. Optionally vitamin supplements maybe administered with the compounds of the present invention.

The invention also refers to a process for preparing a composition as described above, comprising mixing a pharmaceutically active compound thereof with fatty acid or a fatty acid salt or a mixture of a fatty acid salt with a fatty acid and one or more pharmaceutically acceptable diluents and/or carriers.

The invention also provides the use of the above composition in the manufacture of a medicament for the treatment and prevention of obesity. Additionally, it provides the above compositions for use in the treatment and prevention of obesity.

In addition, the present invention refers to a method of treatment of obesity in a human in need of such treatment which comprises administration to the human of a pharmaceutically active compound as defined above and a fatty acid or a fatty acid salt or a mixture of a fatty acid and a fatty acid salt, and optionally additional pharmaceutical acceptable excipients.

The invention also refers to the use of a composition as defined above in the treatment and prevention of obesity.

Another embodiment of the present invention refers to a process for preparing a composition as defined above, comprising mixing a pharmaceutically active compound as defined in claim 1 with a fatty acid or fatty acid salt or a mixture of a fatty acid and a fatty acid salt, and optionally, or more pharmaceutically acceptable diluent and/or carrier.

Further the invention refers to a kit for treatment of obesity, said kit comprising a first component which is a lipase inhibitor and a second component which is a fatty acid or fatty acid salt or a mixture of a fatty acid and a fatty acid salt unit dosage forms.

Another embodiment relates to the use of a composition as defined above in the manufacture of medicaments useful for the treatment and prevention of obesity and to a method of treatment of obesity in a human in need of such treatment which comprises administration to the human of a therapeutically effective amount of a lipase inhibitor and a fatty acid or fatty acid salt or a mixture of a fatty acid and a fatty acid salt as defined above.

The invention also refers to a lipase inhibitor and a fatty acid or fatty acid salt or a mixture of a fatty acid and a fatty acid salt as defined above for the treatment and prevention of obesity.

The invention will be better understood by reference to the following examples which illustrate but do not limit the invention described herein.

EXAMPLES

General remarks: All compounds used in the examples are commercially available. Melting points of the mixtures were determined by DSC (differential scanning calorimeter) and hot stage microscopy.

Example 1

Orlistat/fatty Acid Salt

| COMPOSITION I | |
|---|---|
| sodium capyrylate | 40 mg |
| orlistat | 40 mg |
| phosphate buffer (Sörensen), pH 7.4 | 1 ml |

The above composition consists of orlistat/fatty acid droplets in an aqueous solution (pH <8) at 37° C. No crystals are detectable.

Example 2

Orlistat/fatty Acid Salt

| COMPOSITION II | |
|---|---|
| sodium laurate | 50 mg |
| orlistat | 100 mg |
| water | 3 ml |

A suspension was formed by mixing the ingredients in water at 37° C. The pH was adjusted stepwise with 0.1 N HCl. The samples were investigated by light microscopy and the following results were obtained (FIG. 1).

a) >pH 9.4: only orlistat crystals
b) pH 8.54: both orlistat crystals and fatty acid/orlistat droplets
c) <pH 8.15: only fatty acid/orlistat droplets Decreasing pH-values lead to the formation of orlistat/lauric acid/sodium laurate droplets. At pH values of 8.15 and lower, all of the orlistat molecules are present in their liquid form.

DSC (differential scanning calorimeter) of orlistat/fatty acid in water demonstrated that the melting point of orlistat/lauric sodium laurate was shifted to 32° C. in aqueous solution for pH values <8.

Example 3
Orlistat/fatty Acid Salt

| COMPOSITION III | |
| --- | --- |
| sodium oleate | 50 mg |
| orlistat | 100 mg |
| water | 3 ml |

The ingredients were mixed in water at 37° C. After pH adjustment with 0.1 N HCl to pH 7 the orlistat crystals disappeared and orlistat/oleic acid droplets were formed.

Example 4
Orlistat/fatty Acid

| COMPOSITION IV | |
| --- | --- |
| myristic acid | 60 mg |
| orlistat | 120 mg |
| water | 3 ml |

The ingredients were mixed in water at 37° C. Microscopic investigation showed the presence of orlistat/myristic acid droplets; no orlistat crystals were seen.

Example 5
Orlistat/fatty Acid

| COMPOSITION V | |
| --- | --- |
| palmitic acid | 60 mg |
| orlistat | 120 mg |
| water | 3 ml |

The ingredients were mixed in water at 37° C. Microscopic investigation showed the presence of orlistat/palmitic acid droplets; no orlistat crystals were seen.

Example 6
Orlistat/fatty Acid/fatty Acid Salt
Preparation of the fatty acid sodium salt complex:

| COMPOSITION V | |
| --- | --- |
| sodium laurate | 30 mg |
| lauric acid | 30 mg |
| orlistat | 120 mg |
| (water) | (0.1 ml) |

A complex between sodium laurate and lauric acid is formed, which can be achieved by standard procedures, e.g. intensive mixing the substances at elevated Temperatures (>40), with or without the addition of solvents (water, ethanol) or drying of the solubilized fatty acid/fatty acid salt mixture.

The lauric acid/sodium laurate complex is mixed with orlistat by commonly used equipment until homogeneity is achieved. The composition is dried at 30° C. in Vacuum to constant weight.

Exposure of the dried mixture to buffer solutions pH <8 at 37° C. (e.g. artificial gastric juice led to the formation of liquid orlistat-fatty acid droplets.

Example 7
Orlistat/fatty Acid/fatty Acid Salt
Preparation of the fatty acid sodium salt complex:

| COMPOSITION V | |
| --- | --- |
| sodium myristate | 30 mg |
| myristic acid | 30 mg |
| orlistat | 120 mg |
| (water) | (0.1 ml) |

A complex between sodium myristate and myristic acid is formed, which can be achieved by standard procedures, e.g. intensive mixing the substances at elevated Temperatures (>40), with or without the addition of solvents (water, ethanol) or drying of the solubilized fatty acid/fatty acid salt mixture.

The myristic acid/sodium myristate complex is mixed with orlistat by commonly used equipment until homogeneity is achieved. The composition is dried at 30° C. in Vacuum to constant weight.

Exposure of the dried mixture to buffer solutions pH <8 at 37° C. (e.g. artificial gastric juice USP) leads to the formation of liquid orlistat/myristic acid—myristate droplets.

Example 8
Transfer Efficacy of Orlistat/Fatty Acid Salt

Orlistat (4 mg) suspensions stabilized by fatty acid salts (2 mg) were transferred into 5 ml of a 10% oil in water emulsion (pH value 4.5; oil components: olive oil and cream respectively). The dispersion underwent end-over end mixing for a desired period of time. The oil phase was separated by cold centrifugation and the orlistat content in the oil phase was determined by HPLC. For comparison, an adequate experiment was also performed with a suspension of XENICAL®.

Figure 2:
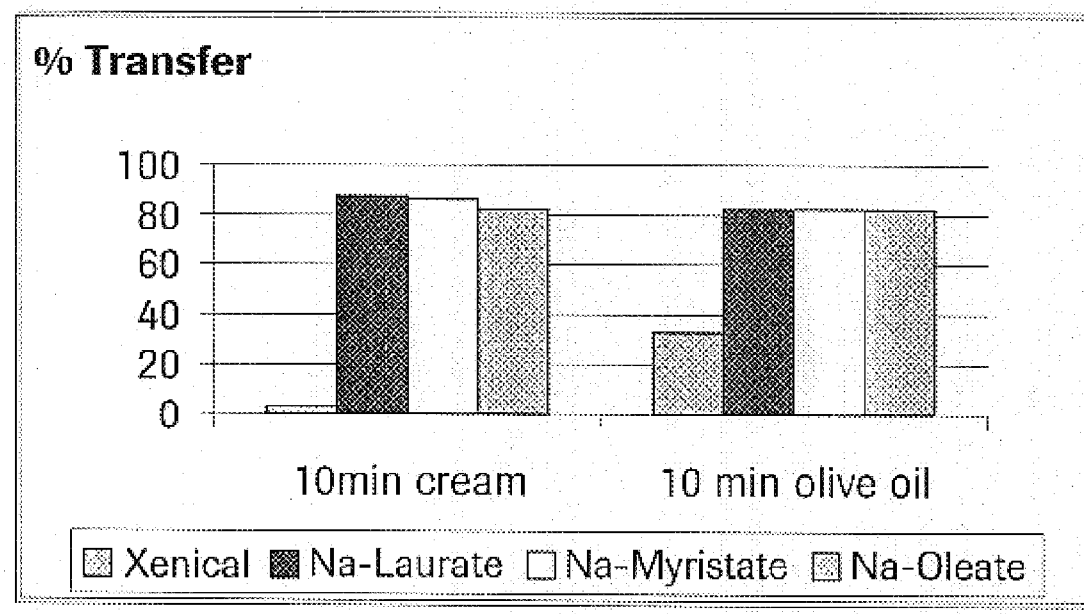
FIG. 2: Orlistat (4 mg) suspensions stabilized by fatty acid salts (2 mg) were transferred into 5 ml of a 10% oil in water emulsion (pH value 4.5; oil components: olive oil and cream respectively). The dispersion underwent end-over end mixing for a desired period of time. The oil phase was separated by cold centrifugation and the orlistat content in the oil phase was determined by HPLC. For comparison, an adequate experiment was also performed with a suspension derived from XENICAL® pellets.

The results indicate (FIG. 2) that in situ forming fatty acid derived orlistat emulsions have a higher efficacy (up to 20-fold) to transfer orlistat into oil compared to XENICAL®. In addition to a general higher transfer efficacy and in contrast to XENICAL®, orlistat is transferred into different kind of oils (cream: emulsified and casein covered oily droplets; olive oil: unprotected oil) at comparable rates. Therefore, a dose reduction and a decreased food dependency can be expected.

Example 9
Chewable Tablet Composition—Fatty Acid—Orlistat

| COMPOUND | AMOUNT |
| --- | --- |
| orlistat | 60 g |
| myristic acid | 30 g |
| mannitol | 400 g |
| lactose | 400 g |
| talcum | 10 g |

Orlistat and myristic acid are melted together at 50° C. Mannitol and lactose are added and the mixture is cooled to RT (room temperature) under continuously stirring. Talcum is added and homogeneously distributed. The powder is pressed into tablets of 960 mg weight (=orlistat content of 120 mg). In vitro release experiments demonstrate the release of orlistat droplets at 37° C. into the following release media: phosphate buffer, pH7.4; citrate buffer, pH 4.5; 0.1 M HCl, pH 1.0.

Example 10
Chewable Tablet Composition—Fatty Acid—Orlistat

| COMPOUND | AMOUNT |
| --- | --- |
| orlistat | 120 g |
| myristic acid | 30 g |
| PEG40-Stearate | 12 g |
| lactose | 15 g |

Orlistat and myristic acid are melted together at 50° C. Sucrosepalmitate and lactose are added and the mixture is cooled to RT under continuously stirring. The powder is pressed into tablets of 960 mg weight (=orlistat content of 120 mg). In vitro release experiments demonstrate the release of orlistat droplets at 37° C. into the following release media: phosphate buffer, pH7.4; citrate buffer, pH 4.5; 0.1 M HCl, pH 1.0.

Example 11
Tablet Composition—Fatty Acid Salt—Orlistat

| COMPOUND | AMOUNT |
| --- | --- |
| orlistat | 120 g |
| sodium laurate | 30 g |
| mannitol | 80 g |
| HPMC 3cp | 60 g |

The ingredients are mixed together with stepwise addition of a (50:50% m/m) ethanol/water mixture (0.2 ml/g). The formed granules are dried in Vacuum at 30° C. to constant weight and pressed into tablets (each containing 120 mg orlistat). In vitro release experiments demonstrate the release of orlistat droplets at 37° C. into the following release media: phosphate buffer, pH7.4; citrate buffer, pH 4.5; 0.1 M HCl, pH 1.0.

Example 12
Tablet Composition—Fatty Acid/Fatty Acid Salt—Orlistat

| COMPOUND | AMOUNT |
| --- | --- |
| orlistat | 120 g |
| myristic acid | 15 g |
| sodium myristate | 15 g |
| mannitol | 80 g |
| HPMC 3cp | 60 g |

The ingredients are mixed together with stepwise addition of a (50:50% m/m) ethanol/water mixture (0.2 ml/g). The formed granules are dried in Vacuum at 30° C. to constant weight and pressed into tablets (each containing 120 mg orlistat). In vitro release experiments demonstrate the release of orlistat droplets at 37° C. into the following release media: phosphate buffer, pH7.4; citrate buffer, pH 4.5; 0.1 M HCl, pH 1.0.

Upon reading the present specification, various alternative embodiments will become obvious to the skilled artisan. These variations are to be considered within the scope and spirit of the subject invention, which is only to be limited by the claims that follow and their equivalents.

What is claimed is:

1. A solid pharmaceutical composition, which comprises:
  a) a solid pharmaceutically active compound that is a lipase inhibitor and has a melting point $\geq 37°$ C., and
  b) a fatty acid or a fatty acid salt or a mixture of a fatty acid and a fatty acid salt;
  the pharmaceutically active compound and the fatty acid or a fatty acid salt or a mixture of a fatty acid and a fatty acid salt being present in amounts such that when the composition is contacted with an aqueous solution having a pH value $\leq 8$, the melting point of the composition is less than the melting point of the solid pharmaceutically active compound and $\leq 37°$ C.

2. The composition according to claim 1, wherein the pharmaceutically active compound is orlistat.

3. The composition according to claim 1, wherein the aqueous solution is buccal or gastric fluid.

4. The composition according to claim 1, wherein the fatty acid or the fatty acid salt or the mixture of a fatty acid and a fatty acid salt is selected from the group consisting of $C_8$ to $C_{24}$ saturated and non-saturated fatty acids, salts of $C_8$ to $C_{24}$ saturated and non-saturated fatty acids, dicarboxylic acids, and salts of dicarboxylic acids.

5. The composition of claim 4, wherein the fatty acid is a $C_{12}$ to $C_{18}$ saturated fatty acid or a salt of $C_{12}$ to $C_{18}$ saturated fatty acid.

6. The composition according to claim 4, wherein the fatty acid or the fatty acid salt or the mixture of a fatty acid and a fatty acid salt is selected form the group consisting of lauric acid, myristic acid, palmitic acid, stearic acid, arachidic acid and behenic acid, and salts thereof.

7. The composition according to claim 6, wherein the fatty acid or the fatty acid salt or the mixture of a fatty acid and a fatty acid salt is selected form the group consisting of lauric acid, myristic acid, and palmitic, and salts thereof.

8. The composition according to claim 7, wherein the fatty acid or the fatty acid salt or the mixture of a fatty acid and a fatty acid salt is selected from the group consisting or lauric acid, myristic acid, and salts thereof.

9. The composition according to claim 4, wherein the fatty acid or the fatty acid salt or the mixture of a fatty acid and a fatty acid salt is selected from the group consisting of $C_{12}$ to $C_{18}$ mono- or polyunsaturated fatty acid and salts thereof.

10. The composition of claim 9, wherein the fatty acid or the fatty acid salt or the mixture of a fatty acid and a fatty acid salt is selected from the group consisting of palmitoleic acid, oleic acid, elaidic acid, erucic acid, linoleic acid, gamma-linolenic acid, alpha-linolenic acid and arachidonic acid, and salts thereof.

11. The composition of claim 10, wherein the fatty acid or the fatty acid salt or the mixture of a fatty acid and a fatty acid salt is selected from the group consisting of oleic acid or linoleic acid and salts thereof.

12. The composition according to claim 4, wherein the fatty acid or the fatty acid salt or the mixture of a fatty acid and a fatty acid salt is a $C_5$ to $C_{24}$ dicarboxylic acid or salt thereof.

13. The composition according to claim 4, wherein the fatty acid or the fatty acid salt or the mixture of a fatty acid and a fatty acid salt is selected from the group consisting of glutaric acid, adipic acid, pimelic acid, suberic acid, azelaic acid, sebacic acid, dodecanedioc acid, and tetradecandioic acid, and salts thereof.

14. The composition according to claim 1, wherein the fatty acid or the fatty acid salt is a mixture of two or more fatty acids or two or more fatty acid salts.

15. The composition according to claim 1, wherein the fatty acid salt is a ammonium, bis(2-hydroxyethyl) ammonium, diethanolammonium, triethanolammonium, sodium, potassium, magnesium or calcium salt.

16. The composition according to claim 15, wherein the fatty acid salt is a sodium or potassium salt.

17. The composition according to claim 1, wherein 0.05 mg to 20 mg fatty acid or 0.05 mg to 20 mg fatty acid salt or 0.05 mg to 20 mg of a mixture of a fatty acid and fatty acid salt is used per 1 mg pharmaceutically active compound.

18. The composition according to claim 17, wherein 0.5 mg to 2 mg fatty acid or 0.5 mg to 2 mg fatty acid salt or 0.5 to 2 mg of a mixture of a fatty acid and fatty acid salt is used per 1 mg pharmaceutically active compound.

19. The composition according to claim 2, wherein the orlistat is present in an amount of 10 to 240 mg.

20. The composition according to claim 19, wherein the orlistat is present in an amount of 30 to 120 mg.

21. The composition according to claim 20, wherein the orlistat is present in an amount of 40, 60, 80, 100, or 120 mg.

22. The composition according to claim 20, wherein the orlistat is present in an amount of 60 to 120 mg and the fatty acid or fatty acid salt or a mixture of a fatty acid and a fatty acid salt is present in the amount of 20 mg to 100 mg.

23. The composition according to claim 22, wherein the orlistat is present in an amount of 120 mg orlistat and the fatty acid or fatty acid salt or a mixture of a fatty acid and a fatty acid salt is present in the amount of 60 mg.

24. The composition according to claim 1 further comprising one or more pharmaceutically acceptable excipients.

25. The composition according to claim 24, wherein the one or more pharmaceutically acceptable excipients are selected from the group consisting of mannitol, lactose, HPMC, talcum, sorbitol, polyvinylpyrrolidone, lecithin, trimyristine, polyethylenglycol, sucrose ester, polysorbate, polyoxethylenstearate, and dimethicon.

26. The composition according to claim 25, wherein the one or more pharmaceutically acceptable excipients are selected from the group consisting of sucrose ester and lactose.

27. The composition according to claim 26, wherein the composition comprises 10–240 mg of orlistat, 0.5–2000 mg of a fatty acid or a fatty acid salt or a mixture of a fatty acid and a fatty acid salt, 5–200 mg of sucrosepalmitate.

28. The composition according to claim 27 further comprising 1.5 g lactose.

* * * * *